Figure 1:
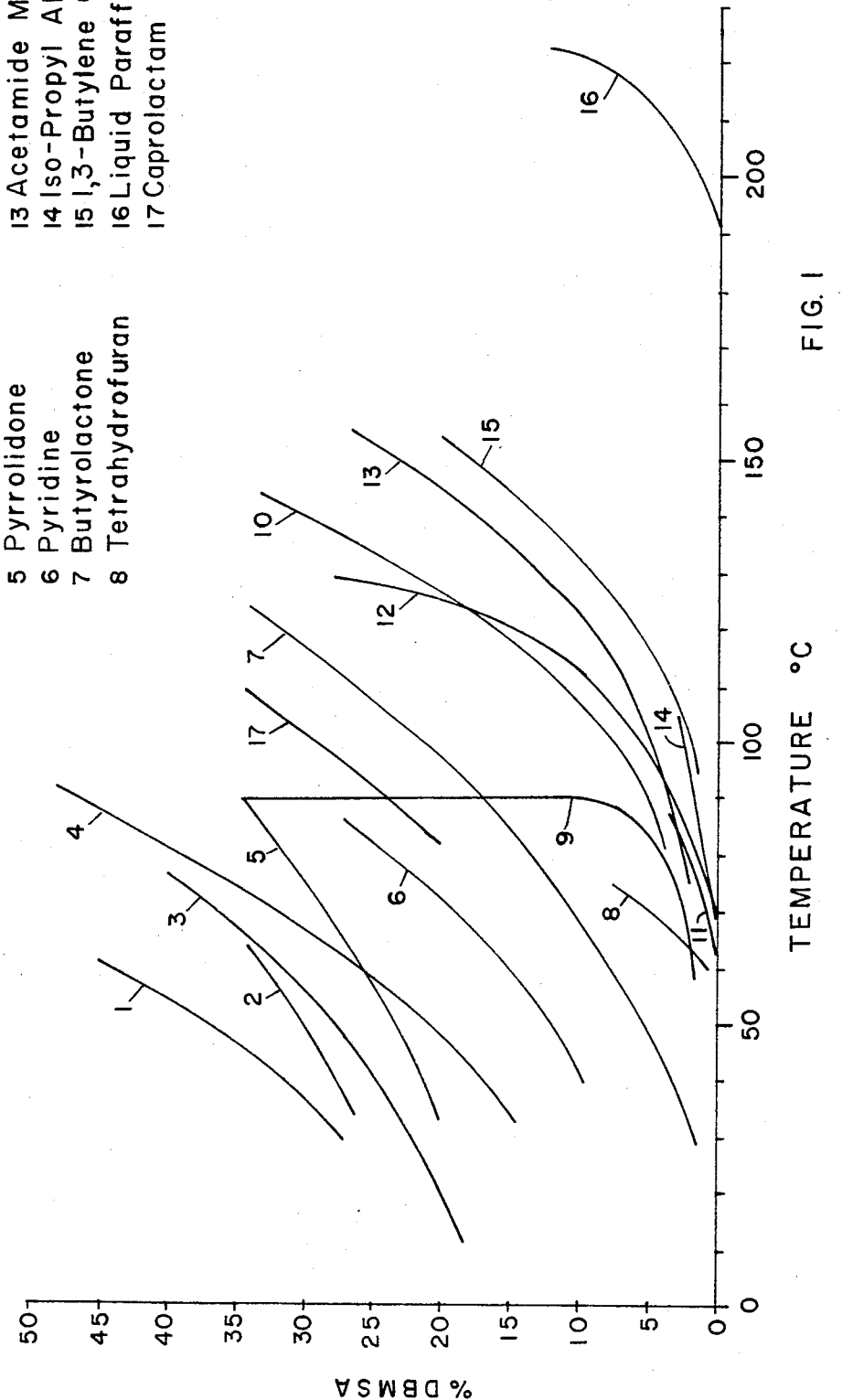

United States Patent [19]

Randhawa et al.

[11] Patent Number: 4,719,102

[45] Date of Patent: Jan. 12, 1988

[54] ACID STABLE DIBENZYL MONOSORBITOL ACETAL GELS

[75] Inventors: Munawar H. Randhawa, Butler; Thomas J. Schamper, Ramsey, both of N.J.

[73] Assignee: American Cyanamid Company, Stamford, Conn.

[21] Appl. No.: 722,748

[22] Filed: Apr. 12, 1985

Related U.S. Application Data

[63] Continuation-in-part of Ser. No. 466,756, Feb. 15, 1983, abandoned.

[51] Int. Cl.⁴ .......................... A61K 7/34; A61K 7/38
[52] U.S. Cl. .............................. 424/66; 424/DIG. 5; 424/68
[58] Field of Search ............... 424/65, 66, 68, DIG. 5

[56] References Cited

U.S. PATENT DOCUMENTS 4,265,878  5/1981  Keil ........................ 424/68
4,346,079  8/1982  Roehl ...................... 424/65

FOREIGN PATENT DOCUMENTS 1365793  5/1964  France ..................... 424/65
48-9984   2/1973  Japan ...................... 424/65
50-52007  5/1975  Japan ...................... 424/70
51-19114  2/1976  Japan ...................... 424/362
0114479   9/1979  Japan ...................... 424/358

Primary Examiner—Dale R. Ore
Attorney, Agent, or Firm—C. J. Fickey

[57] ABSTRACT

A method for producing solid gel antiperspirant sticks at a lower processing temperature, said sticks containing an acidic antiperspirant metal active compound, dibenzyl monosorbitol acetal as the gelling agent and at least one alcohol, wherein a novel solvent is added which is an organic compatible, small compound of not greater than about five carbon atoms and is a good hydrogen bond donor or acceptor, and the gelled antiperspirant sticks formed by the process.

3 Claims, 1 Drawing Figure

ACID STABLE DIBENZYL MONOSORBITOL ACETAL GELS

This application is a continuation-in-part of application Ser. No. 466,756, filed Feb. 15, 1983, now abandoned.

The present invention relates to gelled cosmetic sticks in general. More particularly, it relates to gelled antiperspirant sticks containing an acidic antiperspirant-active compound. Still more particularly, it relates to antiperspirant sticks containing an acidic antiperspirant-active compound in the presence of dibenzyl monosorbitol acetal (DBMSA) and a novel solubilizing agent therefor and to a method for producing said sticks at lower temperatures.

Many known cosmetic sticks consist largely of gelled alcoholic solutions. Sticks which exhibit a desirable transparent or translucent appearance are readily prepared using sodium stearate as the gelling agent: however, they cannot be prepared in the presence of acidic antiperspirant-active salts because the alkaline gelling agent will react with the salt. Opaque sticks are readily prepared from acidic antiperspirant salts using certain low melting waxy materials, such as stearyl alcohol. Translucent gel sticks with dibenzyl monosorbitol acetal have been made containing acidic antiperspirant-active salts but with high temperature processing. The sticks are stable, but there is a need for an easy, low temperature method of making acid-stable, translucent antiperspirant sticks.

Antiperspirant sticks containing dibenzyl monosorbitol acetal and acidic antiperspirant-active salts are disclosed by Roehl, U.S. Pat. No. 4,151,816 (Naarden). These sticks contain, in addition to the salt and gelling agent, a lower monohydric alcohol, such as ethanol; a di- or trihydric alcohol, such as 1,2-propylene glycol or 1,3-butylene glycol, and/or a lower polyglycol; a propylene/ethylene glycol polycondensate, having the formula:

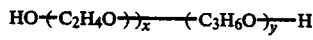

wherein $x/(x+y)$ lies between 0.6 and 1.0 and an average molecular weight of at least 500; and optionally, a mono- or dialkanolamide of a higher ($C_8$–$C_{20}$) fatty acid, such as N-(2-hydroxyethyl)cocamide.

In U.S. Pat. No. 4,346,079, Roehl discloses that a drawback to the sticks described above is their stickiness on application, which can be eliminated by entirely omitting, or greatly reducing, the polycondensate, and adding instead about 0.1 to 25 percent by weight of an oleaginous compound for stickiness control.

Applicants have found that the antiperspirant sticks described by Roehl must be made at elevated temperatures, e.g. at about 140° C. in order to solubilize the dibenzyl monosorbitol acetal with presently used solvents. The use of such elevated temperatures is disadvantageous for a number of reasons.

Forming the stick at such an elevated temperature accelerates the decomposition of the dibenzyl monosorbitol acetal. In addition, specialized equipment is required. Production equipment generally used in the manufacture of antiperspirant is designed to operate at a maximum of about 100° C. Moreover, the use of lower temperatures uses less energy, is safer, poses less vapor problems and will involve lower chemical reaction rates.

A further advantage of lower temperatures is a better compatability with fragrances, lower boiling components, and the plastic packaging into which the heated molten mixture is poured.

It is therefore an object of this invention to provide a composition and method whereby antiperspirant sticks containing dibenzyl monosorbitol acetal and an astringent metal compound may be manufactured at a lower temperature.

Another object is to define a solvent for dibenzyl monosorbitol acetal which is effective at lower temperatures.

These and other objects of my invention will become apparent as the description thereof proceeds.

In accordance with the present invention there are provided antiperspirant sticks containing dibenzyl monosorbitol acetal in the presence of acidic antiperspirant-active salts, said sticks comprising (a) about 1 to 50 percent of a solvent which is a small, polar organic compound; (b) about 1 to 80 percent by weight of a cosolvent (c) about 1 to 10 percent by weight of dibenzyl monosorbitol acetal; (d) about 0 to 35 percent by weight of an emollient; (e) about 5 to 25 percent by weight of an antiperspirant-active compound; (f) about 0 to 2.5 percent by weight of a $C_{12}$–$C_{20}$ fatty acid; and (g) 0.05 to 15 percent by weight of a gel stabilizer; said gel stabilizer being a member of a group consisting of N-(2-hydroxyethyl) fatty ($C_8$–$C_{20}$) acid amides, magnesium sulfate, zinc acetate and hexamethylenetetramine and mixtures thereof.

The novel solvent of the present invention is an organic compatible, small compound and is a good hydrogen bond donor or acceptor. Some suitable compounds fitting within this class are cyclic esters, amides, amines, ketones, ureas, carbamates, sulfoxides and sulfones, and their open chain analogs. Such compounds are small, polar, organic and organic compatible compounds such as lactones, lactams, cyclic ketones, urea, cyclic carbamates, cyclic sulfoxides, cyclic sulfones, or their open chain analogs having no more than 5 carbon atoms. Specifically, compounds such as morpholine, pyridine, acetic acid, ethylene carbonate, propylene carbonate, N-methyl pyrrolidone, pyrrolidone, butyrolactone, dimethylsulfoxide, dimethyl formamide, 2-ethoxyethanol, caprolactam and the like, are included.

Other cosolvents used in the invention are lower substituted alcohols as follows:

Primary or low molecular weight alcohols such as ethanol, n-propanol, n-butanol, 2-methoxyethanol, 2-ethoxyethanol; ethylene glycol, 1,2-propylene glycol, diethylene glycol, and the like, and mixtures thereof. These solvents, because they are primary alcohols or because of their low molecular weight, tend to be more reactive towards dibenzyl monosorbitol acetal in the presence of acidic antiperspirant-active salts. They are, however, excellent solvents for the preparation of the gelled sticks, particularly ethanol. Generally, their useful range if from about 5 to 65 percent by weight.

Alcohol with secondary alcohol groups or longer chain length, for example higher substituted alcohols, are less reactive towards dibenzyl monosorbitol acetal in the presence of acidic antiperspirant-active salts. These are also useful in the present invention. These solvents include isopropanol, isobutanol, diethylene glycol monomethylether, diethylene glycol monoethylether, 1,3-butylene glycol, 2,3-butylene glycol, dipropylene glycol, 2,4-dihydroxy-2-methylpentane, and the like, and mixtures thereof. A generally useful range is about 0 to 70 percent by weight of the stick composition.

The preferred solvents from the above groups are ethanol, either anhydrous or containing up to about 5 percent water, 1,3-butylene glycol and 2,4-dihydroxy-2-methylpentane (sometimes referred to as hexylene glycol).

The stabilizers useful in the present invention to prevent or retard deterioration of the gelled sticks, especially when exposed to elevated temperatures, include N-(2-hydroxyethyl)amides of higher ($C_8$–$C_{20}$) fatty acids, e.g. N-(2-hydroxyethyl)cocamide, magnesium sulfate, zinc acetate, acetamide monoethanol amine and hexamethylenetetramine, and mixtures thereof. One or a combination of these gel stabilizers may be used in the stick compositions of the invention. The amount of stabilizers required will vary and will depend on the relative instability inherent in the solvents used, their relative porportions, and on the acidity of the antiperspirant-active salt used. The N-(2-hydroxyethyl)amides of $C_8$–$C_{20}$ fatty acids and acetamide monoethanol amine will ordinarily be used in an amount ranging from about 1 to 15 percent by weight, perferably about 2 to 6 percent by weight. The magnesium sulfate and zinc acetate stabilizers ordinarily will be used in an amount ranging from 0.2 to 2 percent by weight, preferably about 0.5 to 1 percent by weight, and hexamethylenetetramine ordinarily will be used in an amount ranging from about 0.05 to 0.5 percent by weight, preferably about 0.1–0.2 percent by weight. In general, however, the stabilizer or combination of stabilizers will be used in an amount ranging from about 0.05 to 15 percent by weight, based on the total weight of the stick.

In addition to the solvents, dibenzyl monosorbitol acetal, antiperspirant-active salt and stabilizer, the sticks may contain other commonly used ingredients.

A liquid, volatile cyclic dimethylsiloxane may be added to the compositions to provide a desirable dry feel and emolliency. Other commonly used emollients, such as PPG-3 myristyl ether, octyl isononanoate, and the like, may be incorporated into the stick either in place of or in addition to the dimethylsiloxane. Although optional, it is preferred to use about 3 to 30 percent by weight of one or a combination of emollients.

The antiperspirant-active metal salts used in the present invention are the usual aluminum and/or zirconium compounds, especially aluminum hydroxy chlorides. They may be added in the form of a complex to enhance solubility in alcohols, such as aluminum chlorhydrex or Al/Zr chlorohydrex. The metal salts are effectively used in an amount 10 to 20 percent by weight.

When solutions of aluminum hydroxychlorides are heated there is a tendency towards premature gelation. This may be suppressed by the addition of a small amount of a $C_{12}$–$C_{18}$ fatty acid, such as stearic acid, without adversely affecting the stability of the gel.

In addition to the ingredients described above, the antiperspirant sticks may contain other ingredients in minor amounts, such as a dye color or a fragrance.

FIG. 1 shows a comparison of certain solvents and their capability to dissolve dibenzyl monosorbitol acetal over a range of temperatures. It will be seen that certain solvents are not good in the present invention, although they are used as cosolvents. For example, solvents such as tetrahydrofuran, methyl ethyl ketone, isopropyl alcohol are low boiling and do not solubilize sufficient dibenzyl monosorbitol acetal before being boiled off. Mineral oil is not satisfactory since it has no hydrogen bond interaction. Water is not good, although it is a good hydrogen bond donor and acceptor, because it is not organic compatible The present process involves dissolving the antiperspirant active in one phase and the dibenzyl monosorbitol acetal gellant in another phase. The two phases are then combined and poured into a mold or into the final package. The other components are added to either of the two phases depending on the compatibility of the component with the phases as would be evident to those skilled in the art. If desired, one could employ more phases by forming a separate solution of some of the components. These separate phases then could be added to either of the two main phases or all of the phases could be poured together at the end as for example with a multi stream filling head or in an in-line mixer.

The examples of Table I illustrate this procedure. The antiperspirant active (aluminum chlorhydrex) and stearic acid are dissolved with stirring and heating in absolute ethanol. The final temperature required ranges from room temperature to reflux depending on the particular formulation. The dibenzyl monosorbitol acetal is dissolved in the dibenzyl monosorbitol acetal solubilizing agents (ethanol; acetamide monoethanol amine; propylene carbonate; 1,3-butylene glycol; 2,4-dehydroxy-2-methyl pentane) with stirring and heating. The final temperature determined by the solubility of dibenzyl monosorbitol acetal in the solvent mixture. When the dibenzyl monosorbitol acetal has cleared, the oleaginous materials are added to the dibenzyl monosorbitol acetal phase. The antiperspirant active phase and dibenzyl monsorbitol acetal phase are then combined and poured into the final package or mold.

The following specific examples will illustrate the invention. The examples are shown in tabulated form in Table I.

TABLE I

| EXAMPLE INGREDIENTS | I | II | III | IV | V | VI | VII |
|---|---|---|---|---|---|---|---|
| | | | | Weight Percent | | | |
| DBMSA | 3.0 | 3.0 | 3.0 | 3.0 | 3.0 | 3.0 | 3.0 |
| Ethanol anhydrous | 45.0 | 21.0 | 35.0 | 30.0 | 30.0 | 35.0 | 35.0 |
| Acetamide MEA | 7.0 | 5.0 | 7.0 | 7.0 | 7.0 | 7.0 | 7.0 |
| Propylene Carbonate | 10.0 | 3.0 | 10.0 | 10 | 10 | 15 | 20.0 |
| 1-3 Butylene Glycol | — | 33.0 | — | — | — | — | — |
| Propoxylated Myristyl Ether | — | — | — | 5.0 | 5.0 | — | — |
| Propoxylated Stearyl Ether | — | — | — | — | 10.0 | — | — |
| Silicones (Cyclomethicone) | — | — | 10.0 | 10.0 | — | 5.0 | — |
| Finsolve (Alcohol Benzoate) | — | — | — | — | — | — | — |
| Stearic Acid (Triple Pressed) | — | — | — | — | — | — | — |
| 2,4-Dihydroxy-2-methyl pentane | — | — | — | — | — | — | — |
| Aluminum Chlorohydrex | 15.0 | 15.0 | 15.0 | 15.0 | 15.0 | 15.0 | 15.0 |
| Ethanol Anhydrous | 20.0 | 20.0 | 20.0 | 20.0 | 20.0 | 20.0 | 20.0 |
| Without propylene carbonate, formulations had to be run at 140° C. + see XIII | Processing Temp. 80° C. non-tacky and non-greasy | Processing Temp. 105° C. Slightly tacky and greasy | Processing Temp. 85° C. Non-tacky and non-greasy | Processing Temp. 90° C. Slightly tacky | Same as No. IV | Processing Temp. 85° C. Non-tacky and non-greasy | Processing Temp. 80° C. Non-tacky and non-greasy |

| EXAMPLE INGREDIENTS | VIII | IX | X | XI | XII | XIII |
|---|---|---|---|---|---|---|
| | | | Weight Percent | | | |
| DBMSA | 3.0 | 3.0 | 3.0 | 3.0 | 3.0 | 3.0 |
| Ethanol anhydrous | 42.0 | 30.0 | 25.0 | 25.0 | 25.0 | 27.3 |
| Acetamide MEA | — | 7.0 | 7.0 | 7.0 | 6.5 | — |
| Propylene Carbonate | 20 | 15.0 | 30.0 | 15.0 | 15.0 | — |
| 1-3 Butylene Glycol | — | — | — | — | — | 26.2 |
| Propoxylated Myristyl Ether | — | — | — | — | — | — |
| Propoxylated Stearyl Ether | — | — | — | — | — | — |
| Silicones (Cyclomethicone) | — | 10.0 | — | 15.0 | 15.0 | 5.0 |
| Finsolve (Alcohol Benzoate) | — | — | — | — | — | — |
| Stearic Acid (Triple Pressed) | — | — | — | — | 0.5 | 0.5 |
| 2,4-Dihydroxy-2-methyl pentane | — | — | — | — | — | 3.0 |
| Aluminum Chlorohydrex | 15.0 | 15.0 | 15.0 | 15.0 | 15.0 | 15.0 |
| Ethanol Anhydrous | 20.0 | 20.0 | 20.0 | 20.0 | 20.0 | 20.0 |
| Without propylene carbonate, formulations had to be run at 140° c. + see XIII | Processing Temp. 80° C. Non-tacky and non-greasy | Processing Temp. 80° C. non-tacky and non-greasy | Processing Temp. 70° C. Non-tacky & non-greasy Too Dry After Application | Processing Temp. 80° C. Non-tacky and non-greasy | Processing Temp. 75° C. Non-tacky and non-greasy | Processing Temp. 140° C. |

Additional examples of antiperspirant sticks are shown in Table II. These examples demonstrate the ability to solubilize dibenzyl monosorbitol acetal with various solvents.

The preparation procedure involves dissolving the aluminum chlorohydrex in all but 10% of the ethanol. All of the other ingredients, including the 10% ethanol, with the exception of the octyl isononanoate (or any aleaginous material substituted in its place) are mixed together and heated to affect solution, at which point the octyl isononoate is added. The presence of the ethanol prevents the temperature from rising above its reflux temperature, and, therefore, the vessel should be equipped with a reflux condenser. The two phases are then combined and poured into molds or the final container.

TABLE II

| Example INGREDIENTS | Weight Percent | | | | | | |
|---|---|---|---|---|---|---|---|
| | XIV | XV | XVI | XVII | XVIII | XIX | XX |
| Ethanol (Anhydrous) | 44 | 44 | 44 | 44 | 44 | 44 | 44 |
| Aluminum Chlorohydrex | 15 | 15 | 15 | 15 | 15 | 15 | 15 |
| Dibenzyl monosorbitol acetal | 3 | 3 | 3 | 3 | 3 | 3 | 3 |
| Acetamide MEA (Anhydrous) | 5 | 5 | 5 | 5 | 5 | 5 | 5 |
| Octyl Isononanoate | 13 | 13 | 13 | 13 | 13 | 13 | 13 |
| Propylene Carbonate | 15 | 15 | 15 | — | — | — | — |
| 2-Pyrrolidone | 5 | — | — | 20 | — | — | — |
| N—Methyl Pyrrolidone | — | 5 | — | — | 20 | — | — |
| Butyrolactone | — | — | 5 | — | — | 20 | — |
| Ethylene Carbonate | — | — | — | — | — | — | 20 |

What is claimed is:

1. A solid gelled antiperspirant composition comprising:
   (a) 1 to 50 percent by weight of a solvent which is a small, polar organic and organic compatible compound selected from the group consisting of lactones, lactams cyclic ketones, urea, cyclic carbamates, cyclic sulfoxides, cyclic sulfones, or the open chain analogs thereof, having no more than 5 carbon atoms;
   (b) 0 to 80 percent by weight of a cosolvent alcohol selected from the group consisting of primary or lower substituted alcohols having up to 4 carbon atoms and secondary and higher substituted alcohols having at least 5 carbon atoms;
   (c) 1 to 10 percent by weight of dibenzyl monosorbitol acetal;
   (d) 0 to 35 percent by weight of an emollient;
   (e) 5 to 25 percent by weight of an acidic anitperspirant-active metal salt;
   (f) 0.05 to 15 percent by weight of a gel stabilizer selected from the group consisting of N-(2-hydroxyethyl)fatty ($C_8$–$C_{12}$) acid amide, magnesium sulfate, zinc acetate and hexamethylenetetramine acetamide monoethanol amine and mixtures thereof.

2. The composition of claim 1 wherein said small, polar organic solvent is morpholine, pyridine, N-methyl pyrrolidone, pyrrolidone, acetic acid, ethylene carbonate, propylene carbonate, dimethyl sulfoxide, dimethyl formamide, 2-ethoxyethanol or caprolactam.

3. A composition according to claim 1 wherein the acidic antiperspirant active metal salt is aluminum chlorhydrex or aluminum/zirconium chlorhydrex.

* * * * *